(12) United States Patent
Gu et al.

(10) Patent No.: US 9,011,643 B2
(45) Date of Patent: Apr. 21, 2015

(54) CELLULASE COMPOSITION CONTAINING CELLULASE AND PAPERMAKING POLYMERS FOR PAPER DRY STRENGTH APPLICATION

(71) Applicant: Hercules Incorporated, Wilmington, DE (US)

(72) Inventors: Qu-Ming Gu, Bear, DE (US); Frank J. Sutman, Wilmington, DE (US)

(73) Assignee: Solenis Technologies L.P., Schaffhausen (CH)

( * ) Notice: Subject to any disclaimer, the term of this patent is extended or adjusted under 35 U.S.C. 154(b) by 0 days.

(21) Appl. No.: 14/048,404

(22) Filed: Oct. 8, 2013

(65) Prior Publication Data
US 2014/0174685 A1    Jun. 26, 2014

Related U.S. Application Data

(60) Provisional application No. 61/711,269, filed on Oct. 9, 2012.

(51) Int. Cl.

| | | |
|---|---|---|
| *D21H 17/37* | (2006.01) | |
| *C12N 9/42* | (2006.01) | |
| *D21C 5/00* | (2006.01) | |
| *D21C 9/00* | (2006.01) | |
| *D21H 11/18* | (2006.01) | |
| *D21H 17/00* | (2006.01) | |
| *D21H 17/33* | (2006.01) | |
| *D21H 21/06* | (2006.01) | |
| *D21H 21/08* | (2006.01) | |
| *D21H 21/18* | (2006.01) | |
| *D21H 17/22* | (2006.01) | |
| *D21H 27/30* | (2006.01) | |

(52) U.S. Cl.
CPC .............. *C12N 9/2437* (2013.01); *D21C 5/005* (2013.01); *D21C 9/005* (2013.01); *D21C 9/007* (2013.01); *D21H 11/18* (2013.01); *D21H 17/005* (2013.01); *D21H 17/33* (2013.01); *D21H 17/72* (2013.01); *D21H 21/06* (2013.01); *D21H 21/08* (2013.01); *D21H 21/18* (2013.01); *D21H 17/22* (2013.01); *D21H 17/37* (2013.01); *D21H 27/30* (2013.01)

(58) Field of Classification Search
USPC ........ 162/168.7, 168.2, 164.1, 158, 174, 175, 162/183; 525/328.4; 524/47; 528/335
See application file for complete search history.

(56) References Cited

U.S. PATENT DOCUMENTS

| | | |
|---|---|---|
| 5,169,497 A | 12/1992 | Sarkar et al. |
| 5,423,946 A | 6/1995 | Sarkar et al. |
| 5,507,615 A | 4/1996 | Uno |
| 5,507,914 A | 4/1996 | Sarkar et al. |
| 6,635,146 B2 | 10/2003 | Lonsky et al. |
| 6,770,170 B2 | 8/2004 | Covarrubias |
| 6,939,437 B1 | 9/2005 | Hill, Jr. et al. |
| 2002/0084046 A1 | 7/2002 | Hsu et al. |
| 2004/0038841 A1 | 2/2004 | Koga et al. |
| 2011/0168344 A1 | 7/2011 | Klein et al. |

FOREIGN PATENT DOCUMENTS

| | | |
|---|---|---|
| EP | 1338650 | 8/2003 |
| WO | 2007035481 | 3/2007 |
| WO | 2011130503 | 10/2011 |

OTHER PUBLICATIONS

International Search Report PCT/US2013/063825, p. 1, Nov. 26, 2013.

*Primary Examiner* — Mark Halpern
(74) *Attorney, Agent, or Firm* — Joanne Rossi; Michael Herman

(57) ABSTRACT

Disclosed herein are cellulase compositions useful as papermaking performance additives for improving paper dry strength of a paper product and reducing refining energy in papermaking processes, and improving paper production. These cellulase compositions are formulated using cellulase, papermaking contaminant control polymers, protein stabilizers and cellulase enhancers. These cellulase compositions measure higher in endo-cellulase activity with better stability than conventional cellulase, and have shown differentiating performance in improving paper dry strength properties versus cellulase alone.

10 Claims, No Drawings

CELLULASE COMPOSITION CONTAINING CELLULASE AND PAPERMAKING POLYMERS FOR PAPER DRY STRENGTH APPLICATION

This application claims the benefit of U.S. provisional application No. 61/711,269, filed 9 Oct. 2012, the entire contents of which are hereby incorporated by reference.

FIELD OF THE INVENTION

The present invention relates to a cellulase composition comprising mono-component-endo-cellulases; cationic fixatives and/or nonionic detackifying polymers; cellulase protein stabilizers; and cellulase enhancers. The present invention also relates to the use of a cellulase composition to improve dry strength properties of a paper product by treating cellulosic fibers in pulp furnish by using the cellulase composition at an endo-cellulase activity of from about 5 ECU to about 2500 ECU per kilogram (kg) of dry fiber prior to mechanical refining in a papermaking process.

BACKGROUND OF THE INVENTION

Cellulase can be used to modify the cellulase surface of cellulosic fibers enhancing the efficiency of mechanical refining of wood fiber saving refining energy in papermaking. While the combined action of the cellulase treatment followed by mechanical refining of cellulosic fiber helps in fibrillating the fiber, many commercial cellulases also contain specific cellulase activities that are capable of defibrillating cellulosic fiber by hydrolyzing the fibrillated area on the fiber surface. This action of cellulase is detrimental for paper dry strength properties as the fibrillated area is needed for better fiber to fiber interaction in a paper product upon drying and providing better dry strength. In addition, those specific cellulase activities mentioned above may be capable of hydrolyzing small cellulosic fiber debris or fine particles. While this property of cellulase can help reduce pulp viscosity and improve pulp drainage; it can also cause fiber loss with increased chemical oxygen demand (COD) in paper production. It is not mechanistically clear how a cellulase product can be applied to a papermaking process for improving dry strength properties of a paper product.

Cellulase is generally referred to as an enzyme composition derived from a microorganism fungi or bacteria that can catalyze the hydrolysis of β-1, 4-glycosidic bonds of a cellulase molecule or its derivatives. As shown in Table I, endo-cellulases, exo-cellulases and cellobiase cellulases are three types of specific cellulases that have distinctive activity that is different from each other towards specific cellulase molecules. The three types of cellulases are physically, chemically and enzymatically different. Among them, endo-cellulase or β-glucanase randomly hydrolyzes internal amorphous anomalies within crystalline cellulase, yielding high oligosaccharides or shortened cellulase polysaccharides. Exo-cellulases or exo-cellobiohydrolase (CBH1 or CBH2) release oligosaccharides of a degree of polymerization (DP) of 2 to 4 from the reducing end or non-reducing end of a cellulase polymer. Cellobiase or β-glucosidase has no activity towards cellulase polymer or oligosaccharides but catalyzes the hydrolysis of cellobiase to glucose. Cellulases are used in a variety of industries and are produced in large scale from various species such as *Trichoderma, Humicola, Thermomyces, Bacillus*, etc . . . via genetic enzyme engineering.

To determine endo-cellulase activity in a cellulase product, a water soluble cellulase derivative such as carboxymethyl cellulose (CMC) or hydroxyethyl cellulose (HEC) is conventionally used as a substrate and the reducing sugar released by the enzyme is measured by a dinitrosalicylic acid (DNS) method. The exo-cellulase activity may be distinguished from the endo-cellulase activity by using water insoluble cellulase such as cellulase filter paper or wood fiber as a substrate and the reducing sugar released from the insoluble fiber is then determined by the DNS method mentioned above. The cellobiase activity in a cellulase product is usually determined using cellobiose as a substrate, and the amount of glucose released is assayed using a glucose oxidase (GO) method.

TABLE I

Classification of Cellulase

| Cellulase | Name | Enzyme Nomenclature | Enzyme Assay |
|---|---|---|---|
| Endo-Cellulase | β-Glucanase | E.C.3.2.1.4 | CMC or HEC as substrate, and use the DNS method to measure the reducing sugar content |
| Exo-Cellulase | Exo-Cellobiohydrolases (CBH1 and CBHII) | E.C.3.2.1.91 | Cellulosic fiber as substrate, and use the DNS method to determine reducing sugar released |
| Cellobiase | β-Glucosidases | E.C.3.2.1.21 | Cellobiose as substrate, using the Glucose Oxidase method to determine glucose released |

A cellulase derived from microorganisms may contain all three types of cellulases. While such a product can work synergistically to attack crystalline cellulase and convert it to small sugars, and eventually to glucose, it is not preferred for use in papermaking applications to improve paper dry strength. The endo-cellulase activity in the cellulase product attacks the amorphous anomalies within the crystalline cellulase and disrupts the crystalline structure. This enhances the efficiency of mechanical refining in fibrillating cellulosic fiber and helps improve dry strength of a paper. However, the exo-cellulase activity that exists in the cellulase product may defibrillate the cellulosic fiber and generate cellulase fines. In theory exo-cellulase activity may help improve pulp drainage via defibrillation, but it could also have a negative effect on paper dry strength properties. Not all cellulases are effective for paper strength applications and some can actually hurt the dry strength properties.

A cellulase derived from a microorganism may have multiple components with more than one endo-cellulase and exo-cellobiohydrolase. For example, a cellulase from *Trichoderma longibrachiatum* can have two CBH components, CBH I and CBH II, and three endo-cellulase components, EG I, EG II and EG III. A mono-component cellulase can be produced by the cloning of a specific cellulase DNA sequence encoding the single cellulase and expressed in a host organism. In other words, a mono-component endo-cellulase is a single endo-cellulase component essentially free of other cellulases such as exo-cellulases and β-glucosidase that usually exist in a cellulase product produced by a conventional microorganism. Single endo-cellulases can be used in the present invention for improving dry strength of a paper product in papermaking.

U.S. Pat. Nos. 5,169,497, 5,423,946, 6,770,170, 6,939,437, and U.S. Patent Appl. No. 20110168344, disclose that a cellulase product can be used to improve drainage of a wood pulp when used in combination with cationic polymers. However, the references are silent on how those combinations affect paper dry strength, which specific cellulases may be used in the application or how the cellulase dosage affects the performance for paper dry strength.

U.S. Pat. No. 5,507,914 (the '914 patent), describes a process for enhancing pulp freeness and also paper strength using a combination of a cellulase with a cationic polymer. The '914 patent teaches a dosage level of 0.05-0.25% cellulase based on the dry pulp was used. This is equivalent to about 2500 ECU/kg to about 12500 ECU/kg dry fiber based on the present invention. Our studies indicate that at these higher addition levels, dry strength properties are negatively impacted.

U.S. Pat. No. 6,635,146 (the '146 patent), discloses a method of treating papermaking wood fibers using a one or more truncated hydrolytic enzyme in amounts of 5,000 ECU to 200,000 ECU per kilogram of fiber.

U.S. Patent Appl. No. 20020084046 (the '046 application), describes a process for making paper by adding an enzymatic material to a storing stage that is subsequent to the pulping or refining stage for a paper product having improved softness, bulk and absorbency while maintaining strength.

General literature teaches that cellulase activity may be improved in an enzyme assay when used in combination with anionic and non-ionic surfactants. The possible mechanism is that the surfactants reduce cellulase adsorption to non-cellulase components such as lignin, free cellulase for the cellulosic substrate and aid in thermal stability of the cellulase protein. Tween 20 and Tween 80 are two examples of such surfactants. Polyethylene glycol and its surfactant derivatives may also help improve cellulase activity in cellulase assays. However, little information is available in public on using combination of cellulase and surfactants in papermaking application and how those combinations would affect specific activities of the three different types of cellulases.

U.S. Patent Appl. No. 20040038841 discloses a cellulase formulation produced from nonionic surfactants together with endo-glucanases derived from Zygomycetes, which can be used in the treatment of fabrics.

Japanese Patent No. 5507615 discloses a polyvinyl alcohol and polyvinylpyrrolidone) in a cellulase formulation to enhance cellulase activity.

The publications listed above are all incorporated herein by reference.

DETAILED DESCRIPTION OF THE INVENTION

The present invention relates to a cellulase composition for papermaking comprising: cellulase; contaminant control polymer(s), wherein the contaminant control polymer can be cationic fixative polymer(s), detackifying polymer(s), and mixtures thereof; cellulase protein stabilizer; and cellulase enhancer.

The cellulase composition of the present invention exhibits improved cellulase activity and storage stability over the original cellulase.

In another embodiment, the present invention relates to the use of a cellulase composition to improve dry strength properties of a paper product by treating cellulosic fibers in a pulp, stock or furnish with a cellulase composition prior to mechanical refining in a papermaking process. Mechanical refining of cellulosic plant substances (e.g., wood) is used in the papermaking process to generate pulp, the basis and raw material for making paper products. Pulp is generated by removing cellulase fibers from their wood matrix. This can be accomplished by using chemicals, heat, and pressure, e.g. chemical pulping, or mechanical energy, heat, and pressure, e.g. mechanical pulping. Additionally, individual pulp fibers can be liberated from recycled fiber or dry finished pulp, e.g. market pulp, through application of mechanical energy while slurrying in water. This resulting material can be termed as pulp, pulp slurry, stock or furnish, which terms are used interchangeably and are understood to mean a suspension of cellulosic fiber either before or after mechanical refining. Mechanical refining as used herein refers to treatment of a pulp slurry largely made-up of individual pulp fibers rotating between metal bar-containing discs in a stock refiner. This mechanical action develops fibrillated microstructure on the surface of individual fibers, which allows better bonding to each other upon sheet consolidation and drying. This type of refiner is a common unit operation in paper mills.

Dependent upon the type of paper or paperboard being produced, a papermaker will refine the pulp to a desired freeness. "Freeness" refers to the measurement of water drainage from pulp or the ability of a pulp and water mixture to release or retain water or drainage. Pulps having greater freeness values are characterized as being faster draining, coarser pulps. Freeness is typically reported as Canadian Standard Freeness (CSF). Freeness is dependent upon both the mechanical properties of the refiner and the physical properties of the wood chips. An operator may vary the parameters of the refiner to attain a freeness target. The target or desired freeness is dependent upon the grade of paper or paperboard being produced.

Cellulases used in the present invention are available from any one of several enzyme producers. They can be either mono-component or multiple-component cellulase products. A mono-component endo-cellulase is a cellulase product essentially free of exo-cellulases and cellobiase. Examples of mono-component endo-cellulase include, but is not limited to, FiberCare® R and FiberCare® U from Novozymes (Bagsvaerd, Denmark), Optimase® CX 56L from DuPont Industrial Biosciences (Palo Alto, Calif., USA) and EcoPulp® R from AB Enzymes (Fort Mill, S.C., USA). Examples of multi-component cellulases include, but are not limited to, FiberCare® D, Celluclast® 1.5L from Novozymes and Optimase® CX 40L from DuPont Industrial Biosciences.

The endo-cellulases, exo-cellulases and cellobiase cellulases are known in the art to act synergistically toward cellulosic fibers converting them to glucose. In papermaking, cellulosic fiber may be modified by a specific endo-cellulase with minimal effect on fiber length. It is generally accepted that paper dry strength lies primarily in the bonds between the cellulase fibers and fiber length. Similar to mechanical refining, fiber fibrillation by endo-cellulases creates larger surface area with strong inter-fiber interaction, resulting in lower permeability of the paper product and improved paper dry strength and stiffness. A multi-component cellulase product derived from a microorganism may be employed in this invention. However, if the cellulase contains a significant amount of exo-cellulases, that could function in defibrillating the cellulosic fiber thereby having a negative effect on paper dry strength. Endo-cellulases and mono-component cellulases that are free of any exo-cellulases can be used for improving dry strength properties of a paper product. It should be noted that a multi-component cellulase may exhibit higher cellulase activity in the DNS cellulase assay as described in the experimental section, and it could be more effective than a mono-component cellulase for treating wood pulp to improve pulp drainage.

The contaminant control polymer(s) of the present cellulase composition may contain one or more papermaking detackifying polymer(s) including, for example, nonionic and anionic detackifiers, hydrophobically end-capped poly (ethylene glycol), poly(vinyl alcohol-vinyl acetate), whey protein, soy protein, hydrophobic/hydrophilic block copolymers, and hydrophobically modified hydroxyethyl cellulose (HEC). Commercially available nonionic detackifiers are available from Ashland Inc, Wilmington, Del., USA, among others. Nonionic detackifiers include, but are not limited to, DeTac® DC779F, DeTac® DC3970, and DeTac® DC7225. Anionic detackifiers such as, DeTac® DC720 are also envisioned. In addition to the ability of stabilizing and enhancing endo-cellulase activity, the detackifiers of the present cellulase composition also provide benefits of controlling pitch and stickies deposits in a papermaking process.

The contaminant control polymer(s) of the present cellulase composition may also be one or more papermaking cationic fixative polymer(s), for example, poly(DADMAC) (poly(diallyldimethylammonium chloride), poly(DMA-EPI-EDA) (dimethylamine-epichlorohydrin-ethylenediamine condensation polymers), cationic poly(acrylamide), GPAM (glyoxylated polyacrylamide), poly(ethyleneimine), epichlorohydrin (EPI)-reacted poly(amidoamine), poly(vinylamine), hydrophobically modified cationic polymers such as, alkylated polyethyleneimine (PEI), alkylated poly (lysine), alkylated homo- and co-polymers of vinylamine, alkylated poly(aminoamide), alkylated polyacrylamide, copolymers of vinylamine containing amino groups with hydrophobic monomers, copolymers of dimethyl diallyl ammonium chloride with hydrophobic monomers, copolymers of acrylate containing amino groups with hydrophobic monomers, and alkylated amino containing natural and modified polysaccharides, alkylated cationic proteins and mixtures thereof, C8-C10 alkyl glycidyl ether modified poly(aminoamide), cationic natural products, and amphoteric polymers having a specific cationic unit and an anionic unit such as amphoteric acrylamide polymer formed from both anionic and cationic monomers, the amphoteric vinylamine polymer formed from both anionic and cationic monomers, an amphoteric dimethyl diallyl ammonium chloride derivative, poly(acrylamide-co-acrylic acid-co-dimethyl allyl ammonium chloride copolymer), poly(acrylic acid-co-dimethyl diallyl ammonium chloride copolymer), amphoteric starch, amphoteric polysaccharides, amphoteric polymeric microparticle polymer, and mixtures thereof. Cationic fixative polymers for the use in the present invention are commercially available from Ashland Inc, Wilmington, Del., USA, among others, and include, for example, Zenix DC® 7429, Zenix® DC7479, Hercobond® 6363, Hercobond® 6350 and DeTac® DC786C. The cationic fixative polymers and contaminant control detackifiers can be used separately or together in the cellulase composition. Furthermore, a separate cationic polymer product with contaminant control properties can be applied to a papermaking system in conjunction with the present cellulase composition to improve overall performance.

Additionally, other additives used in the papermaking process can be used in conjunction with the present cellulase composition including, for example, cationic papermaking additives such as, dry strength additives, wet strength additives, flocculants, retention aids, and drainage aids. These cationic papermaking additives may possess fixative properties for anionic components in a papermaking process.

The present cellulase composition also contains cellulase protein stabilizers including, for example, propylene glycol, glycerol, ethylene glycol, sugar, sorbitol, lactic acid, glucose, galactose, maltodextrin, oligosaccharides, corn syrup, and inorganic salts such as, sodium and potassium chloride; a pH buffer system such as, sodium or potassium phosphates, sodium citric acid, tris(hydroxymethyl)methylamine (Tris), 4-2-hydroxyethyl-1-piperazineethanesulfonic acid (HEPES), piperazine-N,N-bis(2-ethanesulfonic acid), 2 2-(N-morpholino)ethanesulfonic acid, and protein ligands such as, glucose and N-acetyl-D-glucosamine, and other protein stabilizers that are well known in the art to stabilize a protein tertiary structure and help maintain enzyme activity.

The cellulase composition of the present invention may also contain one or more metal ion salts that enhance cellulase stability and activity. Metal ion salts include, for example, calcium chloride, zinc chloride and magnesium chloride.

In one embodiment the cellulase composition is a mono-component endo-cellulase and the contaminant control polymer is a polyvinyl acetate-co-vinyl alcohol), hydrophobically end-capped polyethylene glycol detackifier or a mixture thereof; the cellulase stabilizer is propylene glycol, glycerol, sorbitol or mixtures thereof; and the enhancer is calcium chloride.

In yet another embodiment, the cellulase composition is a mono-component endo-cellulase; the contaminant control polymer(s) is a cationic fixative polymer(s) such as, poly (DADMAC), poly(DMA-EPI-EDA), hydrophobically modified cationic fixative or mixtures thereof; the cellulase stabilizer is propylene glycol, glycerol, sorbitol or mixtures thereof; and the cellulase enhancer is calcium chloride.

The ratio of the four main components in the cellulase composition can be changed in a specific range to provide optimized cellulase activity and protein stability under specific pH, ionic strength and temperature conditions. The ratio may also affect its cellulase efficiency of treating cellulosic fibers for paper dry strength applications and the performance of the papermaking contaminant control polymers in a papermaking system. The cellulase composition of the present invention is an aqueous formulation containing up to about 95% water and from about 5% to about 50% other non-aqueous components.

In one embodiment, the cellulase composition has an active concentration of a mono-component endo-cellulase of from about 2 wt. % to about 80 wt. % of the total composition on an active basis; can be about 3 wt. % to about 40 wt. % of the total composition on an active basis; and may be from about 5 wt. % to about 25 wt. % of the total composition on an active basis; the contaminant control polymer concentration can be from about 2 wt. % to about 50 wt. % on an active basis; can be about 5% to about 40 wt. % on an active basis; and may be 10 wt. % to 20 wt. % on an active basis; the protein stabilizer content can be from about 0.1 wt. % to about 50 wt. % on a non-aqueous or dry basis; can be from about 5 wt. % to about 40 wt. % on dry basis; and may be from about 10 wt. % to about 30 wt. % on dry basis. The cellulase enhancer can be from 0.1 wt. % to about 0.5 wt. % on dry basis; can be from 0.001 wt. % to 0.25 wt. % on dry basis; and may be from about 0.005 wt. % to about 0.1 wt. % on dry basis.

In another embodiment, the cellulase composition has an active concentration of a multi-component cellulase of from about 2 wt. % to about 80 wt. % of the total composition on an active basis; can be about 3 wt. % to about 40 wt. % of the total composition on an active basis; and may be from about 5 wt. % to about 25 wt. % of the total composition on an active basis; the contaminant control polymer concentration can be from about 2 wt. % to about 50 wt. % on an active basis; can be about 5% to about 40 wt. % on an active basis; and may be 10 wt. % to 20 wt. % on an active basis; the protein stabilizer content can be from about 0.1 wt. % to about 50 wt. % on a non-aqueous or dry basis; can be from about 5 wt. % to about 40 wt. % on dry basis; and may be from about 10 wt. % to about 30 wt. % on dry basis. The cellulase enhancer can be from 0.1 wt. % to about 0.5 wt. % on dry basis; can be from 0.001 wt. % to 0.25 wt. % on dry basis; and may be from about 0.005 wt. % to about 0.1 wt. % on dry basis.

The active percentages of the contaminant control polymer, the protein stabilizer and cellulase enhancer in the cellulase composition are defined as non-aqueous parts of these polymers or chemicals in the cellulase composition. The active weight percentage of the endo-cellulase or cellulase active in the cellulase composition is based on the assumption that the original cellulase is 100% active as it is obtained from a commercial source.

The pH of the cellulase composition of the present invention affects the stability of the protein stabilizer and activity of the cellulase enzyme. The proper pH prevents protein denaturation that can result in deactivation of the cellulase. The pH of the present cellulase composition can be in the range of from about 3 to about 10; can be in the range of from about 4 to about 8, and may be in the range of from about 5 to about 7. Typically, in a process of producing the present cellulase composition, the contaminant control polymer can be mixed with the protein stabilizer and the cellulase enhancer in water for about 5 to about 30 minutes at room temperature followed by the addition of the mono-component endo-cellulase product. The four components can be added together in a random sequence prior to introduction into the papermaking furnish of the papermaking process. The pH of the cellulase composition can be adjusted with an acid or an alkali if needed after the composition becomes homogenous in appearance. A buffer system may also be used to control the pH of the cellulase composition in a specific range.

The cellulase composition of the present invention exhibited improved cellulase activity relative to the cellulase activity of a conventional composition. The present cellulase composition also had better cellulase storage stability and better physical storage stability relative to the original cellulase, particularly at higher temperatures of about 50° C. or higher. The term "improved cellulase storage stability" means that the present cellulase composition after being stored for a period of time at a certain temperature and subjected to the same standard test conditions as the conventional cellulase, exhibits a lower reduction in cellulase activity compared with that of the original cellulase. The term "good physical stability" means that the cellulase composition has maintained desired physical properties in appearance, homogeneity and light color with no deteriorated odor.

For the cellulases intended to be used in the present cellulase compositions, the cellulase activity including endo-cellulase (ECU) activity, exo-cellobiohydrolases and β-glucosidases activity were tested using standard methods as described in Table I. The endo-cellulase (ECU) activity of the original cellulase measured by DNS assay, as described in the experimental section, is in the range of from about 500 ECU/g to about 20000 ECU/g; can be from about 1000 ECU/g to about 15000 ECU/g; and may be from about 2000 ECU/g to about 10000 ECU/g. The cellulase activity can vary with specific batches of cellulase products, and the materials from different commercial sources. The endo-cellulase activity of the cellulase composition of the present invention is normally in the range of from about 25 ECU/g to about 10000 ECU/g; can be from about 50 ECU/g to about 5000 ECU/g; and may be from about 100 ECU/g to about 3000 ECU/g. The cellulase activity of the cellulase composition may be evaluated under specific pH and temperature conditions with different cellulase substrates as needed. The activities of the cellulase composition of the present invention and the original cellulase with respect to producing reducing sugar from a water soluble cellulase derivative and the reducing sugar from a water insoluble cellulosic fiber were compared to determine the selectivity of the cellulase as an endo-cellulase towards a fiber. The present cellulase composition as a specific endo-cellulase produces higher reducing sugars from a water soluble cellulase derivative and lower reducing sugars from a water insoluble cellulosic fiber than the original cellulase composition. Optionally, cellobiase activity in a cellulase product may be determined using a glucose oxidase (GO) method to measure glucose generated from cellobiose by the cellulase product and compared with that of a known endo-cellulase. The lower the cellobiase and exo-cellulase activity, the more pure the cellulase composition it is as an endo-cellulase product.

The present cellulase compositions may be used in papermaking processing for treating all types of cellulosic fibers including bleached and unbleached virgin fiber, mechanical fiber and recycled fiber, and can be used for virgin fiber and good quality recycled fiber in paper mills that use refiners. The modification of the surface of cellulosic fibers by the present cellulase composition results in a reduction of energy consumption of the mechanical refiner. To evaluate the effectiveness of a cellulase composition on the cellulosic fiber in a practical application in papermaking, one should be able to observe the same refining efficiency with lower refiner energy, improved dry strength properties of the paper product and the change in drainages of the pulp slurry before and after the refiner. In general, a combination of an increased freeness or drainage in the pre-refining pulp and a decrease or unchanged freeness of the post-refining pulp is an indication of effective treatment by the cellulase composition.

One embodiment of the present invention is the process of making a paper product wherein a cellulosic fiber in an aqueous suspension that is being agitated is treated with a cellulase composition comprising a mono-component endo-cellulase; contaminant control polymer(s) such as, detackifiers and/or cationic fixative polymer(s), or mixtures thereof; cellulase protein stabilizer; and cellulase enhancer and the cellulase activity is from between about 5 ECU and about 2500 ECU per kg of dry fiber at a temperature of from about 20° C. to about 70° C. and a pH of from about 4 to about 9 and wherein the cellulase composition is in contact with the cellulosic fiber for at least 10 minutes prior to the cellulosic fiber being refined by a refiner and forming and drying the fiber into a desired product.

Another embodiment of the present invention is the process of making a paper product wherein a cellulosic fiber in an aqueous suspension that is being agitated is treated with a cellulase composition comprising a multi-component cellulase; contaminant control polymer(s) such as, detackifiers and/or cationic fixative polymer(s), or mixtures thereof; cellulase protein stabilizer; and cellulase enhancer and the cellulase activity is from between about 5 ECU and about 2500 ECU per kg of dry fiber at a temperature of from about 20° C.

to about 70° C. and a pH of from about 4 to about 9 and wherein the cellulase composition is in contact with the cellulosic fiber for at least 10 minutes prior to the cellulosic fiber being refined by a refiner and forming and drying the fiber into a desired product.

The mono-component endo-cellulase and the cellulase composition of the present invention can be used for paper dry strength applications in a specific endo-cellulase activity dosage range. Overdosing with a cellulase composition may cause damage to the cellulosic fiber by shortening the fiber length, resulting in reduced bond strength. The dosage of an endo-cellulase needs be controlled at a level that it will not defibrillate the fiber too much and not shorten the fiber length. Surprisingly, it was found that the present cellulase composition made with nonionic detackifiers had little or no negative effect on dry strength properties, such as the Mullen Burst test, in an overdose situation. However, when a detackifier was used with the original cellulase composition a decrease in Mullen Burst was observed. This indicates that the present cellulase composition is much more tolerable in a practical application when the paper furnish is accidentally overdosed due to situations such as, paper machine shutdowns or other unexpected events in a paper mill.

The cellulase composition of the present invention made from a multi-component cellulase containing majorly endo-cellulase activity may be also used for paper dry strength applications. It should be noted that treating virgin or recycled fiber with this composition could generate more cellulosic fines than a mono-component endo-cellulase composition does at the same overall cellulase active due to the presence of exo-cellulase components. Further the multi-component cellulase composition may be more prone to hurt strength property when it is overdosed.

Another embodiment relates to a process of making paper products by treating cellulase fiber in an aqueous solution that is agitated during contact with the cellulase composition comprising at least about 5 ECU of cellulase activity per kg of cellulosic dry fiber.

Another embodiment relates to a process of making a paper product by treating cellulase fibers in an aqueous suspension with a cellulase composition. A cellulase composition according to the present invention is added to a paper furnish that is undergoing agitation. The cellulase composition comprising an amount not to exceed about 2500 ECU of cellulase activity per kg of cellulosic dry fiber; can be from about 20 ECU to about 2000 ECU of cellulase activity per kg of cellulosic dry fiber; and may be about 50 ECU/kg to about 1500 ECU of cellulase activity per kg of cellulase dry fiber.

The pH in the process of making a paper product with the present cellulase composition is at least about pH 3 but not to exceed a pH of about 9; the pH can be from about 4 to about 8.5; and may be from about 4.5 to about 8. Contact time of the cellulase composition with cellulosic fiber is at least about 10 minutes and can be up to about 5 hours; can be from about 0.2 to about 3 hours; and may be from about 0.3 hours to about 2 hours. Temperature is at least 10° C. but not higher than about 70° C.; can be from about 23° C. to about 60° C.; and may be in the range of from about 30° C. to about 50° C. The pulp slurry or furnish temperature in a papermaking system varies with paper machines and specific paper grades. Therefore, it is often expected that the cellulase composition has higher activity in a papermaking system that has higher stock temperature. The selectivity or specificity with regard to the endo-cellulase activity vs. exo-cellulase activity of a specific cellulase composition of the present invention may also change in paper mills that have different system stock pH.

In yet another embodiment, a method of improving the drainage of a cellulosic fiber in a papermaking process is provided. A cellulase composition is provided containing cellulase, contaminant control polymer(s), and mixtures thereof; cellulase protein stabilizer(s); and cellulase enhancer(s), wherein the cellulase composition is added to a pulp slurry in an amount in cellulase activity ranging from about 5 ECU/kg to about 2,500 ECU/kg dry wood fiber.

In the present process the cellulase composition may be used to treat virgin cellulosic fiber, for example, softwood bleached kraft (SWBK), hardwood bleached kraft (HWBK), or a mixture thereof. The present cellulase composition can also be used to treat recycled fiber. In a lab setting, the treatment can be conducted under effective agitation at about 50° C. for about 60 minutes. The treated cellulosic fiber is then subjected to a laboratory refiner such as a PFI mill or valley beater to a desired freeness. The refined pulp is then used to prepare a paper product, such as, handsheets at a specific basis weight. Paper dry strength properties such as Mullen Burst, Dry Tensile, etc . . . are tested and the data normalized based on the basis weight over a blank (the fiber has not been treated with a cellulase composition) and a control using the original cellulase. In addition to improving dry strength, the present cellulase composition may be used to treat virgin or recycled fiber to improve drainage and retention with or without mechanical refining. The present cellulase composition may also be applied to cellulosic fiber after refining and prior to the paper product being formed.

Contaminant control polymers such as detackifiers or cationic fixative polymers are generally used in a papermaking process for cleaning contaminants from cellulosic fibers and paper machine surfaces. One advantage of blending a contaminant control polymer such as, a nonionic and anionic detackifier and/or cationic fixative polymer into the cellulase composition is to help remove stickies adhered on the surface of cellulosic fibers and allow better access of the endo-cellulase to the fiber. The cationic fixative polymer may also interact with the anionic group on the fibers surface thus interrupting hydrogen bonding between cellulosic fibers in the crystalline structure. Additionally, the cationic fixative polymer may help the cellulase penetrate into the fiber wall.

Treating a recycled pulp containing stickies and pitches with the present cellulase composition improved pulp drainage and cellulase efficiency towards the cellulosic fiber. In some cases, the mono-component endo-cellulase and contaminant control polymers had a synergistic effect providing improved paper dry strength properties. When a contaminant control polymer was introduced into the present cellulase compositions, better fiber retention was observed than was seen with the original cellulase. Additionally, the present cellulase composition would be expected to have a positive effect on the chemical oxygen demand (COD) reduction in a paper mill The contaminant control polymers are compatible to the endo-cellulase of the present invention and forms homogenous and stable aqueous compositions with the cellulases.

The present cellulase composition may be used in combination with other papermaking performance additives including cationic, anionic, amphoteric, non-ionic synthetic compounds, and natural polymers. Examples of compounds suitable for use with the present cellulase composition include, but are not limited to, dry strength additives such as, starch, starch derivatives, polyacrylamide derivatives, guar, poly(vinylamine); wet strength additives such as, polyethyleneimine, urea formaldehyde resin, epichlorohydrin reacted poly(aminoamide), starch aldehyde, GPAM; flocculants; coagulants; drainage aids; retention aids; sizing agents; adhesives; debonders; creping adhesives; plasticizers; and modifiers. Individual components of any of the above combinations may be applied together or sequentially in papermaking. Additionally, individual components of any of the above combinations may be blended together prior to use.

In another embodiment, the cellulase composition is combined with a poly(vinylamine) derivative improving pulp freeness and enhancing dry strength properties of a paper product. Poly(vinylamine) interacts with the cellulosic fiber that is already treated by cellulase and refined by mechanic refining via flocculation to preserve the fibrillated cellulase structure and improve pulp drainage. Cellulosic fiber may be attacked by the impurity of exo-cellulase activity in an endo-cellulase product, resulting in producing fiber debris or cellulase fine particles and causing a reduction in total or fine fiber retention in a papermaking process. It was found that a cationic papermaking additive with a high cationic charge density such as, a poly(vinylamine), could be used in a combination with the present cellulase composition to maintain good total fiber retention.

The present cellulase composition can be present in or introduced into a pulper during the pulping stage, or brought into contact at any stock storage chest, high consistency chest or other holding tank. It can also be added into the paper machine white water or, alternatively, can be applied in the water treatment loops of virgin or recycling mills to treat wood fiber. However, addition of the cellulase composition should be at least 10 minutes before the mechanical refiner, allowing contact time of the cellulase composition with the cellulosic fiber. Effective agitation or mixing is needed if the cellulase is to have an effective action on the fiber. Pulp consistency also contributes to the effectiveness of the treatment by the cellulase composition. High pulp consistency reduces mass-transfer efficiency, resulting in non-uniform interactions between the cellulase and fiber. Low pulp consistency decreases the concentration of the cellulase in the pulp at a fixed cellulase/dry fiber ratio and reduces cellulase efficiency. In general, the pulp consistency of the cellulase fiber treated by the cellulase composition is at least about 0.3% and should not exceed about 10%. The pulp consistency can be in the range of from about 1% to about 5%; and may be in the range of from about 2% to about 4%.

Treating the pulp slurry using a combination of the present cellulase composition with one or more other enzymes may achieve an enhanced performance in pulp drainage and dry strength properties of a paper product. Such enzymes typically include hydrolases such as, hemicellulases, amylases, proteases, lipases, esterases, and pectinases; lyases such as, pectate lyase. Additionally, other enzymes may be used in combination with the present cellulase composition. Other enzymes include oxidoreductases, such as, laccase, lignin oxidase, glucose oxidase, and peroxidases. These enzymes can be used in any form, such as liquid, gel or solid form. Individual enzymes or any combinations of different enzymes may be applied together with the present cellulase composition, or applied sequentially before or after the addition of the present cellulase composition. Individual enzymes may be also blended together with the present cellulase composition to form a blended composition prior to use.

The following examples further illustrate the present invention and are not intended to be in any way limiting to the scope of the invention as claimed.

Cellulase Assays
Reducing Sugar Estimation by Dinitrosalicylic Acid (DNS) for Endo-Cellulase Activity The endo-cellulase activity assay was performed using 1% carboxymethyl cellulose (CMC, M7F, Ashland, Wilmington Del., USA) as the substrate, in 0.1 Molar (M), pH 7.0 sodium phosphate buffer. The reducing sugar was determined using a dinitrosalicylic acid (DNS) method, in which dinitrosalicylic acid is reduced to 3-amino-5-nitrosalicylic acid under alkaline conditions producing a color that is then measured spectrometrically at a UV absorbance of 540 nm. Glucose was the standard for the calibration. One endo-1,4-$\beta$-glucanase unit (ECU) is defined as the amount of cellulase producing one micromolar ($\mu$mol) of reducing sugars as glucose from CMC in one second at pH 7.0.

In a typical example, 0.2 grams (g) of a 0.1% solution of the cellulase composition (equivalent to approximately 0.1 ECU to 0.15 ECU of cellulase) was added to 1.8 g of a CMC solution (1.0%, pH 7.0) in a test tube. The mixture was incubated with shaking at 50° C. for 10 minutes, after which, 3 milliliters (ml) DNS reagent (freshly prepared according to Miller, G. L. 1959, Analytical Chemistry 31, p. 426), was added to the mixture and the resulting mixture heated in boiling water for exactly 5 minutes. The solution in the test tube was cooled to room temperature and UV absorbance at 540 nm was measured. The standard curve (UV 540 nm vs. glucose concentration) was established simultaneously using 0.1% glucose with the same DNS test reagents.

In general, the endo-cellulase activity (ECU) of the present cellulase composition was in the range of from about 60 ECU/g to about 3600 ECU/g cellulase solution using the above assay under the specific conditions.

Measurement of CMC Viscosity Reduction to Determine Relative Endo-Cellulase Activity This method was used to determine relative endo-cellulase activity in percentage of the present cellulase composition compared with the original cellulase. In this method, a viscous solution of carboxymethyl cellulose (CMC, M7F) was incubated at 40° C. with a sample of cellulase composition. The degradation of CMC resulted in reduced viscosity of the solution. To be accurate, the final viscosity should be measured at least 40% and not exceed 60% of the original viscosity. The degree of the decrease in the viscosity is proportional to the endo-cellulase activity. The viscosity of a CMC solution containing the original cellulase and a CMC solution containing the present cellulase composition were measured using a DV-E or DV-II Viscometer (Brookfield Viscosity Lab, Middleboro, Mass.) at a selected spindle (number 3) and speed (30 rpm). The units are in centipoises (cps).

As an example, 60 grams of CMC solution (2.6% in 0.1 M sodium phosphate buffer at pH 7.0, with Brookfield viscosity around 1500 cps) was prepared and the viscosity was measured (Vo-sample). The solution was heated to 40° C. and maintained at 40° C. for 5 minutes, and a small amount of cellulase (equivalent to approximately 1 ECU to 2 ECU of cellulase) as a 1.0% solution in 0.1 M sodium phosphate buffer at pH 7.0 was added. The resulting mixture was incubated with agitation at 40° C. for 10 minutes and the mixture was cooled to 23° C. and the viscosity measured (Ve-sample). The same analysis was conducted with the original cellulase with the same batch of the CMC solution as used with the present cellulase composition. The viscosity of the starting solution and the end solution were measured as Vo-standard and Ve-standard respectively. The relative cellulase activity of the sample was calculated as (Vo-sample−Ve-sample)=100/(Vo-standard−Ve-standard).

Relative Exo-Cellulase Activity Using the Dinitrosalicylic Acid (DNS) Method

An amount of the present cellulase composition (equivalent to approximately 2 ECU/g to 3 ECU/g dry fiber) was added to cellulosic fiber suspended in water at pH 7.0 forming a pulp slurry. The resulting slurry was incubated at 50° C. for 8 hours. The pulp was filtered off and the reducing sugar content in the filtrate was determined by the DNS method described previously. One milliliter (ml) of the filtrate was incubated with 4 ml DNS reagent in boiling water for exactly 5 minutes. The sample was cooled to room temperature and the UV absorbance at 540 nm measured. A standard curve was established simultaneously using the DNS test method referred to above and a 0.1% glucose solution at varying concentrations.

Protein Assay

Protein concentration of the present cellulase compositions were determined using a Bio-Rad Protein Assay Method, which is a dye-binding assay based on a method developed by M. M. Bradford (see Bradford M. M., "A rapid and sensitive method of determining microgram quantities of protein utilizing the principle of protein-dye binding", Analytical Biochemistry 72:248-254, 1976). An acidic dye reagent is added to a protein solution and the UV absorbance of the solution was measured at 595 nm with a UV spectrometer. Comparison of these results to the bovine serum albumin (BSA) standard curve provides a relative measurement of protein concentration. A Bio-Rad protein assay reagent was obtained from Bio-Rad Laboratories. As a standard procedure, the dye reagent was freshly prepared by diluting 1 part of the Bio-Rad protein assay dye reagent with 4 parts of water. Five dilutions of BSA standard were prepared in a linear range from 0.2 milligrams per milliliter (mg/ml) to 0.9 mg/ml. In the test, 100 microliters (μl) of the BSA dilutions and the protein sample of an unknown concentration were pipetted into test tubes and 5 ml of the diluted dye reagent was added to the protein sample. The mixtures in the test tubes were vortexed and incubated at room temperature for 10 minutes, and the UV absorbance was measured at 595 nm.

The protein assay was used to measure protein content as a percentage of the cellulase composition and the specific cellulase activity was determined. In general, the protein concentration in weight percentage of the present cellulase composition was in the range of from about 0.02% to about 1%.

EXAMPLE 1

Formulating the Cellulase Composition

This example illustrates a general method of preparing the present cellulase composition using an endo-cellulase or a multi-component cellulase; a contaminant control polymer, a cellulase protein stabilizer; and a cellulase enhancer.

A homogenous solution was prepared by sequentially adding a contaminant control polymer, a cellulase protein stabilizer and a cellulase enhancer to a desired amount of water at a temperature of about 20° C. with constant stirring forming a homogenous solution. A solution of cellulase was slowly added to the homogenous solution over a 20 minute time period at a temperature not exceeding 28° C. resulting in mixtures according to the Examples found in Table II. The temperature of each mixture was taken to 20° C. and agitated for 20 minutes. The pH of each mixture was then adjusted to 6 using HCl or NaOH as needed, to obtain a homogenous and transparent cellulase composition. The active percentages of the contaminant control polymer, the protein stabilizer and cellulase enhancer in the present cellulase composition are defined as non-aqueous parts of these polymers or chemicals in the cellulase composition. The active weight percentage of the endo-cellulase or cellulase active in the present cellulase composition is based on the assumption that the original cellulase is 100% active as it is obtained from a commercial source. The Bio-Rad protein assay was occasionally performed to determine the protein concentration of the cellulase composition and to verify the active percentage of the original cellulase in the cellulase composition.

EXAMPLE 2

Cellulase Activity of the Cellulase Compositions

Example 2, demonstrates improvements in endo-cellulase activity of the present cellulase compositions compared with the original cellulase compositions. In this experiment, a mono-component endo-cellulase in the form of FiberCare® R and a multi-component cellulase in the form of FiberCare® D were used.

The contaminant control polymers used for the cellulase compositions are all commercially available from Ashland Inc, Wilmington, Del., USA. Cationic fixative polymers used in the experiment included Zenix® DC7429 and Zenix® DC7479. The hydrophobically modified cationic fixative was DeTac® DC786C, and nonionic papermaking detackifiers DeTac® DC779F and DeTac® DC3970 were also used.

The mono-component endo-cellulase used in the present cellulase compositions (Example 2-3 to Example 2-9) was also used in Comparative Example 1 and Examples 2-1 to 2-2, as shown in Table II. Additionally, all of the cellulase compositions used in this study were prepared fresh and tested after one day stored at room temperature. Results as summarized in Table II, indicate that the contaminant control polymers enhanced the action of cellulase activity toward CMC substrate.

The multi-component cellulase used in the present cellulase compositions (Example 2-10 to Example 2-11) was also used in Comparative Example 2, as shown in Table II. The results indicate that the contaminant control polymers, Zenix® DC7429 and DeTac® DC3970, enhanced the action of cellulase activity toward CMC substrate.

TABLE II

Cellulase Activity of the Cellulase Compositions

| Examples | Description of the Preparations | ECU/g (DNS) | Relative Activity (CMC viscosity) |
|---|---|---|---|
| Comparative Example 1 | 15% Mono-component endo-cellulase | 750 | 100% |
| Comparative Example 2 | 15% Multi-component cellulase | 1875 | 370% |
| Example 2-1 | 15% Mono-component endo-cellulase, 11% propylene glycol, and 11% glycerol | 740 | 101% |
| Example 2-2 | 15% Mono-component endo-cellulase, 11% propylene glycol and 11% glycerol, 0.05% calcium chloride | 810 | 114% |

TABLE II-continued

Cellulase Activity of the Cellulase Compositions

| Examples | Description of the Preparations | ECU/g (DNS) | Relative Activity (CMC viscosity) |
|---|---|---|---|
| Example 2-3 | 15% Mono-component endo-cellulase, 15% Zenix ® DC7429, 3.5% propylene glycol, and 3.5% glycerol, 0.05% calcium chloride | 820 | 128% |
| Example 2-4 | 15% Mono-component endo-cellulase, 30% Zenix ® DC7429, 0.05% calcium chloride | 820 | 120% |
| Example 2-5 | 15% Mono-component endo-cellulase, 15% Zenix DC ® 7479, 3.5% propylene glycol and 3.5% glycerol, 0.05% calcium chloride | 825 | 122% |
| Example 2-6 | 15% Mono-component endo-cellulase, 15% DeTac ® DC786C, 3.5% propylene glycol and 3.5% glycerol, 0.05% calcium chloride | 805 | 115% |
| Example 2-7 | 15% Mono-component endo-cellulase, 12% DeTac ® DC779F, 0.05% calcium chloride | 820 | 119% |
| Example 2-8 | 15% Mono-component endo-cellulase, 5% DeTac ® DC779F, 8.5% propylene glycol and 8.5% glycerol, 0.05% calcium chloride | 815 | 123% |
| Example 2-9 | 15% Mono-component endo-cellulase, 5% DeTac ® DC3970, 8.5% propylene glycol and 8.5% glycerol, 0.05% calcium chloride | 827 | 125% |
| Example 2-10 | 15% Multi-component cellulase, 15% Zenix DC ® 7429 | 2081 | 426% |
| Example 2-11 | 15% Multi-component cellulase, 15% DeTac ® C3970 | 1988 | 444% |

Table II, also illustrates improved endo-cellulase activity of the present cellulase composition containing a small amount of calcium chloride (Example 2-1) vs. the same composition without calcium chloride (Example 2-2).

EXAMPLE 3

Cellulase Stability of the Cellulase Compositions

Example 3, demonstrates that the present cellulase compositions formulated with papermaking contaminant control polymers were more stable than the original cellulase compositions in endo-cellulase activity after storage. The relative endo-cellulase activity of the present cellulase composition was determined as percentage of the original cellulase after stored at 50° C. for 46 days and a CMC viscosity reduction method was used to test relative activity as described below.

The relative activity of a conventional endo-cellulase composition stored in a refrigerator (Comparative Example 1 at 4° C.) was measured and used as a control reference as 100% active. It should be noted that all the assays were performed using the same cellulase active. It should also be noted that the difference between cellulase activity vs. cellulase active in a cellulase composition is that the term "cellulase activity" is referred to as the cellulase activity as measured by the DNS and CMC viscosity reduction assays while the "cellulase active" is referred to by the weight percentage of a commercial cellulase product in the cellulase composition, and a commercial or conventional or original cellulase is usually considered 100% active as it is.

TABLE III

Cellulase Stability of Cellulase compositions

| Examples | Description of the preparations | Time (days) | Temp. (° C.) | Relative Activity (CMC viscosity) |
|---|---|---|---|---|
| Comparative Example 1 | 15% Mono-component endo-cellulase | 46 | 4 | 100% |
| Comparative Example 1 | 15% Mono-component endo-cellulase | 46 | 50 | 54% |
| Example 2-2 | 15% Mono-component endo-cellulase, 11% propylene glycol and 11% glycerol, 0.05% calcium chloride | 46 | 50 | 67% |
| Example 2-3 | 15% Mono-component endo-cellulase, 15% Zenix ® DC7429, 3.5% propylene glycol and 3.5% glycerol, 0.05% calcium chloride | 46 | 50 | 98% |
| Example 2-5 | 15% Mono-component endo-cellulase, 15% Zenix DC ® 7479, 3.5% propylene glycol and 3.5% glycerol, 0.05% calcium chloride | 46 | 50 | 94% |
| Example 2-6 | 15% Mono-component endo-cellulase, 15% DeTac ® DC786C, 3.5% propylene glycol and 3.5% glycerol, 0.05% calcium chloride | 46 | 50 | 86% |
| Example 2-7 | 15% Mono-component endo-cellulase, 12% DeTac ® DC779F, 0.05% calcium chloride | 46 | 50 | 81% |
| Example 2-8 | 15% Mono-component endo-cellulase, 5% DeTac ® DC779F, 8.5%% propylene glycol and 8.5% glycerol, 0.05% calcium chloride | 46 | 50 | 85% |

As shown in Table III, the present cellulase composition (Example 2-3, 2-5, 2-6, 2-7 and 2-8) retained more than 81% of the original cellulase activity after being stored at 50° C. for 46 days. The cellulase composition in the absence of a papermaking contaminant control polymer had an activity of only 54% of the conventional composition. Two cellulase compositions (Example 2-3 and 2-5) formulated with Zenix® DC7429 and Zenix DC® 7479 exhibited more than 90% of the original cellulase activity and were more active than the original cellulase (Comparative Example 1) after storage.

Cellulase can undergo protein denaturation and deactivation quickly at higher temperatures of 50° C. or higher. Therefore, shelf-life of a cellulase product is one factor to consider for large-scale industrial applications, particularly during hot summer months. The present cellulase compositions have shown improved stability at high temperatures. Physical stability was also monitored and it was observed that the present cellulase compositions listed in Table III remained homogenous and transparent without sedimentation or any color and odor development over 46 days.

EXAMPLE 4

Dry Strength of Handsheets Made from Virgin Fiber

Example 4, demonstrates improvement in dry strength properties of handsheets made from a virgin fiber that had been treated by the present cellulase composition vs. the fiber treated by the original cellulase. Softwood bleached kraft (SWBK) was pulped in water at 3% consistency and then treated with both the present cellulase compositions and the original cellulases. The original cellulase was used as a control and was used at the same dosage of the cellulase active at 50° C. for 1 hour under effective agitation as the cellulase composition of the present invention. The cellulase active dosage of the control at 0.1% vs. dry fiber was equivalent to approximately 750 ECU per kg of dry pulp. The treated SWBK pulp was then blended with hardwood bleached kraft (HWBK) pulp furnish that had been made down to 3% consistency at a 30/70 (SWBK/HWBK) weight ratio. The resulting virgin fiber pulp had a freeness of 530 Canadian Standard Freeness (CSF) and was refined to 480-490 CSF by a laboratory valley beater using TAPPI Test Method 200 sp-01.

Paper handsheets having a basis weight of 25 lb./3000 sq. ft. were made on a Noble and Wood handsheet machine at pH 7.0. The Handsheets were wet pressed to 33% solids and dried on a drum drier at 240° F. for 1 minute giving a moisture content of 3% to 5%. Dry tensile (TAPPI Test Method T494, om-01) and Mullen Burst (TAPPI Test Method T403) were determined. The dry strength properties of the handsheets made with the present cellulase compositions were compared with handsheets made with the original cellulase in the absence of the contaminant control polymers (Example 2-2, as a control). Dry tensile and Mullen Burst properties of the handsheets can be seen in Table IV and are expressed as % versus the control.

TABLE IV

Dry Strength Performances of the Cellulase Compositions

| Examples | Description of the preparations | Dosage (wt. % based on fiber) | Dry Tensile % | Mullen Burst % |
|---|---|---|---|---|
| Example 2-2 | 15% Mono-component endo-cellulase, 11% propylene glycol and 11% glycerol, 0.05% calcium chloride | 0.1 | 100 | 100 |
| Example 2-3 | 15% Mono-component endo-cellulase, 15% Zenix ® DC7429, 3.5% propylene glycol and 3.5% glycerol, 0.05% calcium chloride | 0.1 | 105 | 111 |
| Example 2-7 | 15% Mono-component endo-cellulase, 12% DeTac ® DC779F, 0.05% calcium chloride | 0.1 | 108 | 106 |
| Example 2-9 | 15% Mono-component endo-cellulase, 5% DeTac ® DC3970, 8.5% propylene glycol and 8.5% glycerol, 0.05% calcium chloride | 0.1 | 107 | 103 |

Results of Example 4, show that the cellulase composition of the present invention (Example 2-3, 2-7, and 2-9) improved dry strength performance in both Mullen Burst and Dry Tensile strength of the handsheets when compared with the control (Example 2-2). Separate experiments indicated that contaminant control polymers used alone with a cellulase, had no benefit in paper dry strength.

EXAMPLE 5

Effect of Cellulase Dosage on Paper Dry Strength Properties

Mullen Burst of a paper product can vary with treatment conditions and fiber quality. This may be explained by the hypothesis that Mullen Burst is a combination of different paper properties, combining fiber length and inter-fiber bonding. It was found that fiber length within a paper product suffered when the wood pulp was treated with a cellulase composition before refining.

Example 5, demonstrates the dosage effect of a cellulase composition on Mullen Burst as compared with the original cellulase. Example 5, also provides a comparison of the Mullen Burst of a handsheet made with a mono-component endo-cellulase vs. a multi-component cellulase on the dosage effect on a paper product. A 30/70 w/w ratio mix of SWBK/HWBK was pulped in water at 3% consistency forming a suspension or slurry. The temperature of the suspension was adjusted to 50° C. and treated with a cellulase composition at a dosage of 500 ECU to 5500 ECU per kg of dry pulp and agitated for 1 hour. The resulting treated pulp was refined to between about 400 CSF and about 480 CSF by a PFI mill using TAPPI Test Method T-248. Paper handsheets having a 25 lb./3000 sq. ft. basis weight were prepared on a Noble and Wood handsheet machine at pH 7 using the same method as described in Example 3. Mullen Burst of the handsheets made with the present cellulase composition (Example 2-7) were compared with comparative Examples 1 and 2), expressed as percentage versus the blank without any cellulase treatment of the virgin fiber before refining.

TABLE V

Cellulase Dosage Effect of Present Cellulase Compositions vs. Original cellulase Compositions on Mullen Burst of Handsheets

| Examples | Description of the preparation | Dosage wt. % based on fiber | ECU/ kg fiber | Mullen Burst % |
|---|---|---|---|---|
| Comparative Example 1 | 100% Mono-component endo-cellulase | 0.01 | 500 | 114 |
|  |  | 0.02 | 1000 | 111 |
|  |  | 0.04 | 2000 | 106 |
|  |  | 0.1 | 5000 | 103 |
| Comparative Example 2 | 100% Multi-component cellulase | 0.01 | 1250 | 116 |
|  |  | 0.02 | 2500 | 100 |
|  |  | 0.04 | 5000 | 87 |
| Example 2-7 | 15% Mono-component endo-cellulase, 12% DeTac ® DC779F, 0.05% calcium chloride | 0.067 | 549 | 116 |
|  |  | 0.133 | 1091 | 120 |
|  |  | 0.67 | 5490 | 114 |

As shown in Table V, handsheets made using the original cellulase (Comparative Example 1) shows a tendency of decreasing Mullen Burst from a 14% increase to a 3% increase as the cellulase dosage increased from 500 ECU/kg dry fiber to 5000 ECU/kg dry fiber. This tendency in Mullen Burst property is not observed with the cellulase composition of the present invention (Example 2-7), which had a 14% increase in Mullen Burst at a dosage of 5490 ECU/kg fiber and a 20% increase in Mullen Burst at 1091 ECU/kg fiber. The handsheets made from a multi-component cellulase (Comparative Example 2) contained a significant amount of exo-cellulase activity and had a 16% increase in Mullen Burst at 1,250 ECU/kg fiber over the fiber treated with the original cellulase. However, when overdosed at 5,000 ECU/kg fiber with the present composition, Mullen Burst was only 87% of the mono-component cellulase control (comparative Example 2) at comparative dosages.

Example 5, indicates that both the selection of the cellulase type and management of the cellulase activity dosage play a role in paper dry strength application. Overdosing a conventional multi-component cellulase to cellulosic fiber can result in shortened fiber length and reduced dry strength properties. This is particularly true of the Mullen Burst of a paper product, due to the action of the exo-cellobiohydrolase activity that exists in the product. Overdosing a mono-component endo-cellulase to the fiber might cancel out the improvement in paper dry strength properties that is achievable at a lower and proper cellulase activity dosage. In a practical situation the cellulase concentration can build up unexpectedly high in a papermaking system if the white water is recycled in a closed system, or the paper machine is shut down for cleaning and other maintenance. Additionally, Example 5, shows that handsheets made using the present cellulase composition at high cellulase dosages, had no negative effect on Mullen Burst.

Example 6

Dry Strength and Drainage Performance of the Cellulase Composition on Recycled Fiber Example 6, demonstrates improvement in dry strength properties of the handsheet made from recycled fiber treated with both the present cellulase composition and the original cellulase. Recycled fiber from 100% recycled medium was pulped at 3% consistency and treated with the cellulase compositions of the present invention and the original cellulase as a control. Cellulase active dosages of 0.02% based on dry pulp were used. The treatment was conducted at 50° C. for 1 hour under effective agitation. The resulting pulp was refined by a laboratory valley beater using TAPPI Test Method 200 sp-01, for 6 minutes under the same conditions. The freeness was measured before and after the refining. Paper handsheets of 80 lb./3000 sq. ft. basis weight were prepared on a Noble and Wood handsheet machine at pH 7.0. The handsheets were wet pressed to 33% solids and dried on a drum drier at 240° F. for 1 minute to give 3-5% moisture. Dry Tensile (TAPPI Test Method T 494 om-01) and Ring Crush (TAPPI Test Method T822 om-02) of the handsheets were determined. The Dry Tensile and Ring Crush properties were normalized and expressed as % versus that from the Blank.

TABLE VI

Dry Strength Performances of the Present Cellulase Compositions versus Original Cellulase Compositions on High Basis Weight Recycled Paper

| Examples | Description of the preparation | Dosage (wt. % based on fiber) | Pre-refining CSF | Post-refining CSF | Dry Tensile % | Ring Crush % |
|---|---|---|---|---|---|---|
| Blank | None | 0 | 357 | 322 | 100 | 100 |
| Comparative Example 1 | 100% Mono-component endo-cellulase | 0.02 | 415 | 360 | 105 | 115 |
| Example 2-8 | 15% Mono-component endo-cellulase, 5% DeTac ® DC779F, 8.5% propylene glycol and 8.5% glycerol, 0.05% calcium chloride | 0.133 | 425 | 390 | 109 | 114 |
| Example 2-9 | 15% Mono-component endo-cellulase, 5% DeTac ® DC3970, 8.5% propylene glycol and 8.5% glycerol, 0.05% calcium chloride | 0.133 | 433 | 398 | 106 | 123 |

The results as shown in Table VI, demonstrate that the cellulase composition of the present invention (Example 2-9) provided an 8% improvement in Ring Crush and equivalent performance in Dry Tensile relative to the original cellulase (Comparative Example 1). There was almost a 40 CSF freeness improvement of the recycled fiber furnish when the fiber was treated with the cellulase composition of the present invention (Example 2-9) over the fiber that was treated with the original cellulase after mechanical refining. Additionally, an alternate cellulase composition according to the present invention (Example 2-8) gave a 30 CSF freeness improvement to the post refining furnish.

EXAMPLE 7

Recycled Fiber Pulp Drainage

Example 7 demonstrates improvement in pulp drainage by treating recycled fiber with the present cellulase compositions over cellulosic fiber treated with the original cellulase. Recycled pulp slurry was made using 100% recycled medium at 3.3% consistency. The temperature of the slurry was adjusted to 50° C. and treated with a cellulase composition at a dosage of 0.03% cellulase active based on dry fiber, and the treated slurry agitated for 1 hour. The efficiency in drainage of the present cellulase composition was compared with that of the original cellulase and a blank (having no cellulase treatment), using a vacuum drainage test (VDT) as described below. The comparison in drainage efficiency was also conducted in the presence of a cationic poly(vinylamine), Hercobond® 6350 (Ashland Inc, Wilmington, Del., USA), at 0.2% based on the dry pulp. The results are summarized in Table VII.

A vacuum drainage test (VDT) setup is similar to a Buchner funnel test, consisting of a 300-ml magnetic Gelman filter funnel, a 250-ml graduated cylinder, a quick disconnect, a water trap, and a vacuum pump with a vacuum gauge and regulator. The VDT test was conducted by first setting the vacuum to 10 inches Hg and placing the funnel on the graduated cylinder. Two hundred fifty grams of 0.5 wt. % of pulp stock was charged into a beaker and the cationic polymer Hercobond® 6350 was added to the stock while being agitated by an overhead mixer. The stock was then poured into the filter funnel and the vacuum pump was turned on while simultaneously starting a stopwatch. The drainage efficacy is reported as the time (seconds) required to obtain 230 ml of filtrate. The shorter the time the better the pulp drainage.

TABLE VII

Improvement in Recycled Fiber Drainage by the Cellulase Compositions

| Examples | Description of the preparation | Dosage wt. % vs. fiber | Hercobond ® 6350, active % vs. fiber | VDT (second) |
|---|---|---|---|---|
| Blank | None | — | — | 79.5 |
| Comparative Example 1 | 100% Mono-component endo-cellulase | 0.03 | — | 72.4 |
| Comparative Example 4 | DeTac ® DC779F | 0.1 | — | 78.6 |
| Comparative Example 5 | DeTac ® DC3970 | 0.1 | — | 77.8 |
| Example 7-1 | 15% Mono-component endo-cellulase, 5% DeTac ® DC779F | 0.2 | — | 67.7 |
| Example 7-2 | 15% Mono-component endo-cellulase, 5% DeTac ® DC3970 | 0.2 | — | 69.0 |
| Comparative Example 6 | None | — | 0.2% | 63.2 |
| Example 7-3 | Mono-component endo-cellulase | 0.03 | 0.2% | 56.2 |
| Example 7-4 | 15% Mono-component endo-cellulase, 5% DeTac ® DC779F | 0.2 | 0.2% | 49.6 |
| Example 7-5 | 15% Mono-component endo-cellulase, 5% DeTac ® DC3970 | 0.2 | 0.2% | 54.5 |

As shown in Table VII, the recycled pulp treated with the present cellulase composition (Example 7-1 and 7-2) resulted in improved drainage with reduced VDT time of 67.7 seconds and 69.0 seconds respectively, compared to 72.4 seconds when the recycled pulp was treated with the original cellulase (Comparative Example 1) and 79.5 seconds for the blank. The contaminant control polymers (nonionic detackifiers) (Comparative Example 4 and 5) did not reduce the VDT time when used alone. Example 7, suggests a synergistic effect of the mono-component endo-cellulase and nonionic detackifiers for improving drainage of a recycled fiber furnish.

The combination of the present cellulase composition and cationic poly(vinylamine) Hercobond® 6350 (Example 7-4) further reduced the VDT time to 49.6 seconds while the combination of the original cellulase and Hercobond® 6350 (Example 7-3) reduced the VDT time to 56.2, which was about 6-7 seconds longer than Example 7-4. These drainage test results further illustrates that the present cellulase composition provides for increased pulp drainage rates when other cationic papermaking additives are also used.

EXAMPLE 8

Paper Dry Strength Using a Combination of the Cellulase Composition and Poly(vinylamine)

Example 8, demonstrates improved dry strength performance of the present cellulase composition over the original cellulase when the cellulase composition was used in combination with the poly(vinylamine) Hercobond® 6350. A sample of 100% recycled fiber was pulped to a 3% consistency. The resulting pulp slurry was treated with cellulase compositions at a dosage of 0.2% based on dry fiber for 1 hour at 50° C. The resulting treated slurry was then refined using a valley beater for 3 minutes using TAPPI Test Method 200 sp-01. Handsheets of 50 lb./3000 sq. ft. were prepared using the cellulase treated slurry with addition of 0.2% active Hercobond® 6350 based on the dry pulp using the methods described in the previous examples. Experiments were conducted using both the present cellulase composition and the original cellulase at the same cellulase active dosage. Dry Tensile of the handsheets were tested. Additionally, STFI short span compression strength was tested using TAPPI Method T-815. These dry strength properties are expressed as % versus the control without cellulase and Hercobond® 6350.

TABLE VIII

Dry Strength Performances of Combination of Cellulase composition and Poly(vinylamine) on Recycled Paper

| Examples | Description of the preparation | Dosage (%/fiber) | Hercobond® 6350, active % vs. fiber | Dry Tensile % | STFI % |
|---|---|---|---|---|---|
| Blank | None | 0 | 0.2 | 108 | 112 |
| Comparative Example 1 | 100% Mono-component endo-cellulase | 0.03 | 0.2 | 110 | 121 |
| Example 7-5 | 15% Mono-component endo-cellulase, 5% DeTac® DC3970 | 0.2 | 0.2 | 113 | 127 |

The data in Table VIII, indicates that the present cellulase composition (Example 7-5) provides greater improvement in Dry Tensile (113%) and STFI (127%), when used in combination with Hercobond® 6350, than the fiber treated with the original cellulase (Comparative Example 1) under the same treatment conditions. Example 8, also demonstrates the differentiating performance of the present cellulase composition vs. the original cellulase in paper dry strength application.

EXAMPLE 9

Fixative and Retention Properties Using the Cellulase Compositions

Example 9, demonstrates lower turbidity of wood pulp obtained by treating the fiber with the present cellulase composition relative to that by the conventional cellulase, indicating potentially better fiber retention or fixative properties with the present cellulase composition. A virgin fiber mix 30/70 w/w SWBK/HWBK, was pulped to a 3.3% consistency and the resulting pulp slurry treated with the cellulase composition of the present invention and the original cellulases. Treatment was done at the same cellulase active at 50° C. for 1 hour and a pH 7.0 using effective agitation. The treated pulp was cooled to about 25° C. and refined to between about 480 CSF and about 420 CSF by a valley beater using TAPPI Test Method 200 sp-01. The treated pulp slurry was added to a Britt jar with Whatman 541 filter paper and stirred for 5 minutes at room temperature using a mechanical stirrer at 1000 rpm. The pulp was filtered under vacuum and 150 ml of filtrate was collected. A turbidity meter was used to measure turbidity of the filtrate as formazin attenuation unit (FAU). The lower the FAU number, the better the fixative property or retention the pulp has. The turbidity data (FAU) is summarized in Table IX, and the fixative properties of the present cellulase compositions and the original cellulases are also expressed as percentage turbidity of the blank handsheet (the handsheet made with untreated fiber) shown in the last column of Table IX. The lower the percentage, the better fixative properties and retention the handsheet has.

TABLE IX

Reduced Turbidity of Filtrate from Virgin Fiber Treated by Cellulase Compositions

| Products | Descriptions | Dosage (%/fiber) | Turbidity (FAU) | % Turbidity of the blank |
|---|---|---|---|---|
| | None | — | 87 | 100% |
| Comparative Example 1 | 100% Mono-component endo-cellulase | 0.015 | 50 | 58% |
| Example 9-1 | 15% Mono-component endo-cellulase, 15% Zenix® DC7429, 3.5% propylene glycol and 3.5% glycerol | 0.1 | 30 | 35% |
| Example 9-2 | 15% Mono-component endo-cellulase, 15% DeTac® DC786C, 3.5% propylene glycol and 3.5% glycerol | 0.1 | 27 | 31% |
| Example 9-3 | 15% Mono-component endo-cellulase, 5% DeTac® DC779F, 8.5% propylene glycol and 8.5% glycerol | 0.1 | 34 | 39% |

As shown in Table IX, the pulp shiny treated with the present cellulase compositions (Example 9-1 to 9-3) provides filtrates having 20-30% lower turbidity than when treated with the original cellulase (Comparative Example 1). These results indicate that the present cellulase compositions provide better fiber retention than the original cellulases.

What is claimed is:

1. A composition for treating cellulosic fibers used to make paper or paperboard comprising:
    a) cellulase, wherein the active cellulose concentration is from about 2% by wt. of total composition to about 80% by wt. of total composition; and
    b) contaminant control polymer(s);
    wherein the contaminant control polymer(s) are selected from the group consisting of detackifier polymer(s) selected from the group consisting of poly(vinyl alcohol-co-vinyl acetate), hydrophobically end-capped polyethylene glycol, hydrophobically modified hydroxyethyl cellulose, hydrophobic/hydrophilic block copolymers, surface active proteins, whey protein, egg protein, soy protein, and mixtures thereof wherein the detackifier polymer is from about 2% by wt. of total composition to about 50% by wt. of total composition; wherein the active weight percentage of the cellulose active is considered 100% active as obtained from a commercial source.

2. The composition of claim 1, further comprising: cellulase protein stabilizer(s); and cellulase enhancer(s).

3. The composition according to claim 2, wherein the contaminant control polymer is a cationic fixative polymer, a hydrophobically modified cationic polymer, or an amphoteric polymer that are net cationic or mixtures thereof.

4. The composition of claim 2, wherein the cellulase enhancer is a metal ion salt selected from the group consisting of calcium chloride, zinc chloride, and magnesium chloride.

5. The composition according to claim 2, wherein the protein stabilizer content is from 0.1% by wt. of total composition to about 50% by wt. of total concentration, and the cellulase enhancer content is from 0.1% by wt. of total composition to about 0.5% by wt. of total composition; and wherein the active weight percentage of the active cellulase in the cellulase composition is considered 100% active as obtained from a commercial source; and wherein the active percentages of the contaminant control polymer, the protein stabilizer and cellulose enhancer in the cellulase composition are defined as non-aqueous parts of these polymers or chemicals in the cellulase composition.

6. The composition according to claim 2, wherein the protein stabilizer content is from 0% by wt. of total composition to about 50% by wt. of total concentration, and the cellulase enhancer content is from 0% by wt. of total composition to about 0.5% by wt. of total composition;

wherein the active weight percentage of the active cellulase in the cellulase composition is considered 100% active as obtained from a commercial source; and wherein the active percentages of the contaminant control polymer, the protein stabilizer and cellulase enhancer in the cellulase composition are defined as non-aqueous parts of these polymers or chemicals in the cellulase composition.

7. The composition according to claim 2, wherein the cellulase is a mono-component endo-cellulase; the contaminant control polymer is selected from the group consisting of cationic fixative polymer(s), poly(vinyl acetate-co-vinyl) alcohol, hydrophobically end-capped polyethylene glycol or mixtures thereof; the cellulose stabilizer is a propylene glycol, glycerol, sorbitol or mixtures thereof: and the cellulase enhancer is calcium chloride.

8. The composition of claim 1, wherein the cellulase is an endo-cellulase.

9. The composition of claim 8, wherein the endo-cellulase is a mono-component endo-cellulase.

10. The composition of claim 1, wherein the cellulase is a multi-component cellulase.

* * * * *